United States Patent
Heino et al.

(10) Patent No.: US 8,512,379 B2
(45) Date of Patent: Aug. 20, 2013

(54) BIOABSORBABLE BAND SYSTEM, A BIOABSORBABLE BAND, A METHOD FOR PRODUCING A BIOABSORBABLE BAND, A NEEDLE SYSTEM OF A BIOABSORBABLE BAND AND A LOCKING MECHANISM

(75) Inventors: Harri Heino, Tampere (FI); Perrti Törmälä, Tampere (FI); Pertti Vesanen, Toijala (FI)

(73) Assignee: Bioretec Oy, Tampere (FI)

( * ) Notice: Subject to any disclaimer, the term of this patent is extended or adjusted under 35 U.S.C. 154(b) by 1315 days.

(21) Appl. No.: 11/988,937

(22) PCT Filed: Jul. 14, 2006

(86) PCT No.: PCT/FI2006/050342
§ 371 (c)(1),
(2), (4) Date: Jan. 17, 2008

(87) PCT Pub. No.: WO2007/010092
PCT Pub. Date: Jan. 25, 2007

(65) Prior Publication Data
US 2009/0270923 A1    Oct. 29, 2009

(51) Int. Cl.
*A61B 17/70* (2006.01)
*A61B 17/08* (2006.01)

(52) U.S. Cl.
USPC ....................................................... 606/263

(58) Field of Classification Search
USPC ..................... 606/74, 263, 230, 231
See application file for complete search history.

(56) References Cited

U.S. PATENT DOCUMENTS

| | | | | |
|---|---|---|---|---|
| 4,942,875 | A * | 7/1990 | Hlavacek et al. | 606/230 |
| 5,007,939 | A * | 4/1991 | Delcommune et al. | 525/415 |
| 5,089,012 | A * | 2/1992 | Prou | 606/224 |
| 5,462,542 | A * | 10/1995 | Alesi, Jr. | 606/151 |
| 6,200,318 | B1 * | 3/2001 | Har-Shai et al. | 606/74 |
| 7,112,221 | B2 * | 9/2006 | Harris | 623/13.11 |
| 7,648,504 | B2 * | 1/2010 | Heino et al. | 606/74 |
| 7,875,233 | B2 * | 1/2011 | Huang et al. | 264/512 |
| 2004/0173934 | A1 * | 9/2004 | Tunc | 264/178 R |
| 2005/0070928 | A1 | 3/2005 | Heino et al. | |
| 2006/0002979 | A1 * | 1/2006 | Ashammakhi et al. | 424/426 |
| 2007/0032634 | A1 * | 2/2007 | Gale et al. | 528/480 |

FOREIGN PATENT DOCUMENTS
EP        0594176 A    4/1994
EP        0596277 A    5/1994
WO    WO-88/06022 A    8/1988

OTHER PUBLICATIONS

Finish Patent Office Action, dated Mar. 30, 2010, issued in connection with counterpart Finnish Application No. 20086028.
PCT/ISA/210—International Search Report—Dec. 6, 2006.
PCT/IPEA/409—International Preliminary Report Patentability—Sep. 5, 2007.

* cited by examiner

*Primary Examiner* — Kevin T Truong
*Assistant Examiner* — Christopher Beccia
(74) *Attorney, Agent, or Firm* — Venable LLP; Eric J. Franklin

(57) ABSTRACT

A bioabsorbable band system for securing a bone fracture, or an osteotomy, or a soft tissue on a bone. The bioabsorbable band system includes a needle system and a bioabsorbable band including a bioabsorbable locking member. The bioabsorbable band includes a length having an at least partially oriented structure. The bioabsorbable band further includes a locking mechanism with a locking member. Also a method for producing the bioabsorbable band.

4 Claims, 7 Drawing Sheets

US 8,512,379 B2

BIOABSORBABLE BAND SYSTEM, A BIOABSORBABLE BAND, A METHOD FOR PRODUCING A BIOABSORBABLE BAND, A NEEDLE SYSTEM OF A BIOABSORBABLE BAND AND A LOCKING MECHANISM

CROSS-REFERENCE TO RELATED APPLICATIONS

This application claims priority to Finnish patent application 20055416 filed 18 Jul. 2005 and is the national phase under 35 U.S.C. §371 of PCT/FI2006/050342.

FIELD OF INVENTION

The present invention relates to a bioabsorbable band system for securing a bone. The band system comprises a bioabsorbable band including a bioabsorbable locking member and a needle system.

BACKGROUND OF THE INVENTION

In bone surgery it is well known to apply longitudinal implants like bands, braids, or wires to fixation of bone fragments to each others. Such implants are made usually of metals or of polymeric materials.

Chest surgery such as, for example, open heart surgery requires opening of the chest and rib cage in order to facilitate access to the organ to be operated. The front central part of the rib cage constitutes a longitudinal bone, the sternum, which overlies the heart and secures the ribs. A specific action performed in such surgery is longitudinal sectioning of the sternum into two halves ("median sternotomy"). After performing the heart surgery, the chest is closed as a part of a reconstitution operation, in which among other activities the sternum bone halves are brought to union and secured together by mechanical means.

Post operative complications in the healing of the sternum are not uncommon, resulting from several reasons. Especially troublesome is the constant movement associated with the breathing cycle, to which the bone is subjected, which keeps the sternum in a cyclic strain regime often accompanied by unpredicted mechanical stresses. Such strains may eventually cause non-union or breakage of the bone. Nowadays as recuperating procedures for cardiac therapy have become more common, sternal complications have been increasing likewise. Healing disorders can be expected to occur more commonly in patients suffering from bone disorders such as osteoporosis.

Surgical band and locking member systems position cables and locking implants around bones to allow healing. One common form of a locking implant is a crimp system. These systems are used to crush the cable into engagement with the tissue to retain the cable at a desired position. However, current designs of cable and crimp systems, particularly for surgical use, have significant drawbacks. For example, a tension, which is too low or too high may lead to improper healing or to poor medical results.

Also, in many prior art cable and crimp systems there is the possibility for slippage of the cable in the crimp, which can lead to delayed healing. The loosening of the cable, e.g. in bone fracture fixation, can also lead to delayed healing, pain or even to a failure of healing. Also, many prior art crimps cannot be easily locked at a desired tension, and often the desired tension can not be maintained when using a cable loop or winding as there is an inevitable drop in tension when the pliers are removed. Thus, a surgeon typically has to "over shoot" the desired tension, guessing how much of that tension will be lost after the crimping has been completed and the pliers removed, thus significantly increasing the possibility for tensioning errors.

In addition, many prior art crimps are bulky and may cause adverse tensioning in the surrounding tissues, which may result in a negative effect on tissue healing. Another drawback of many prior art cable and crimp systems is that they are made of metal, such as stainless steel. Such extremely stiff materials are mechanically incompatible with bone tissue and therefore, may cause osteolysis below the material, which may lead to implant migration.

SUMMARY OF THE INVENTION

The present invention diminishes the above-mentioned drawbacks of the prior band systems for securing a bone and provides a bioabsorbable band system comprising a needle system and a bioabsorbable band including a bioabsorbable locking member. The bioabsorbable band system provides accurate tensioning of the band and safe locking of the band around a bone. The bioabsorbable band is used for securing a bone fracture, or an osteotomy, or a soft tissue on a bone. The present invention is mainly utilized in the chest surgery. Besides the chest surgery, the present invention is also usable in orthopaedics and traumatology, like in the femoral bone surgery, with tubular bones and in repair of the patella.
General Description The bioabsorbable band comprises a band section and a locking section. The band section is preferably even in its width throughout its length in order to facilitate its pulling through soft tissues around a bone, or through a bone without causing injuries. In the band section there are first locking means which are compatible with second locking means in the locking section. When the band is tightened the first and the second locking means grip to each other in such a manner that the band cannot loosen. To secure the fastening there is a separate or an integrated locking member, which is connected to the locking section.

When the bioabsorbable band is used for securing a bone a needle is attached directly or indirectly to the end of the band section (to the opposite end compared to the locking section). If the locking member is a separate piece it is connected to the locking section in such a manner that the locking member is immediately ready for locking when the band is tight enough for securing the bone. The end of the band section is pulled by the needle around/through the bone and/or the surrounding tissue in such a manner that it is possible to form a loop from the band by threading the other end of the band through the locking section and the locking member, and tighten the band. When the tension of the band is on the desired level the locking member is switched to a locked position and the needle is removed.

The first and second locking means may comprise pawl teeth which are able to grip to each other. Each of the pawl teeth preferably has the same size and shape. The pawl teeth are preferably inclined in such a manner that they have a natural tendency to grip to each other instead of a tendency to separate from each other. In order to form inclined teeth the plane of the locking section in the longitudinal direction of the band may be inclined. Besides the teeth, the first and second locking means may have different constructions but the main idea is that the first and second locking means form counterparts.

The first and the second locking means and the locking member form a locking mechanism. The first and the second locking means grip to each other in order to form a locking, and the locking member secures the locking.

The bioabsorbable band comprises a length having an at least partially oriented structure. It means that the length is completely or partially oriented by drawing at a temperature, which is below the melting point of the polymer but above its glass transition temperature (if any). The drawing is done with a predetermined draw ratio. The (partially) oriented structure may be formed also by inserting an oriented body/bodies in a matrix.

The bioabsorbable band is manufactured in such a manner that the bioabsorbable band with the band section and the locking section is first manufactured, and after that at least a part of the band section is oriented by drawing. The band section may simultaneously be heated. The temperature, in which the band section is simultaneously heated, is between the glass transition temperature and the melting point of the processed material.

The locking section may remain unoriented, or it may also be constructed of an oriented material. The draw ratio in the orientation is 1:1.1 ... 1:10, preferably 1:1.5 ... 1:8. A very useful draw ratio is 1:4-5 for poly a-hydroxy acid polymers and copolymers/terpolymers. It is possible that both the length of the band section and the locking section are oriented but they may have different draw ratios. Naturally, also the same draw ratio is possible. The band section may be oriented throughout its length, or only a certain length is oriented.

The orientation can be brought in to the bioabsorbable band in such a manner that oriented bodies, such as oriented fibers, are inserted in the band. In that case other materials of the band may be unoriented.

According to one solution, the band section of the bioabsorbable band is oriented completely but the locking section is not oriented. At the junction of the band section and the locking section then exists a length having an orientation gradient. In such a manner desirable properties can be achieved to the band section, and manufacturing of the locking section becomes easier. After the orientation the band section has a high strength, a good flexibility and an adequate ductility.

The manufacturing method of the bioabsorbable band may be machining, or moulding. The moulding method is preferably injection moulding or compression moulding. The preferred machining methods are mechanical machining methods. Other possible machining methods are e.g. laser machining and waterjet cutting. Also methods based on rapid prototyping are possible. The first and second locking means, such as pawl teeth, are formed after orientation preferably by machining or compression moulding.

It is also possible that the first and second locking means are formed during the molding process, i.e. a mold, such as an injection mold, is designed so that the first and second locking means, e.g. the pawl teeth, can be formed during the molding process. In such a manner working phases are reduced. After the molding process the band section is drawn to orientate it.

The raw materials of the bioabsorbable band and the locking member are bioabsorbable polymers, copolymers or polymer mixtures or alloys. Generally speaking, the bioabsorbable band including the locking member often comprises polymerized α-hydroxy carboxylic acids. The preferred material of the band and the locking member is polylactide or glycolide/lactide copolymer.

The bioabsorbable band and the locking member may be blended and/or reinforced by ceramic fibers or powders or flakes etc., such as bioabsorbable hydroxyapatite, bioactive glass, or tricalcium phosphate fibers or powders.

According to an advantageous embodiment of the invention, elements of the system, such as a band and/or a locking member, may have a special coating layer on its surface and may contain one or more bioactive substances, such as antibiotics, chemotherapeutic substances, growth factors like bone morphogenic proteins, substances accelerating the healing of the wound and osteotomy, hormones or other drugs and the like. Such bioactive elements are especially advantageous in surgical use, because they contribute biochemically to the healing of the lesion in addition to providing mechanical support.

The implants of the present invention may be sterilized by well known sterilization techniques, depending on the type of material used in manufacturing of the implant. Suitable sterilization techniques include radiation sterilization such as cobalt 60 irradiation or electron beams, ethylene oxide sterilization, and the like.

The needle system comprises a needle and an intermediate element which is intended to be between the needle and the bioabsorbable band. The element is flexible, thus giving freedom of movement to the needle and the band. When the needle and the band are able to move in relation to each other, the concentration of stress to the band or the needle is avoided because the flexible connection element is able to deform. The element may comprise a metallic mesh, a polymeric fabric, or a polymeric band. Also other structures, such as a tubular intermediate element, is possible, but the structure of the intermediate element depends on the shape of the needle and the band. The material of the intermediate element resists higher temperatures than the material of the band. Both bioabsorbable and biostable materials come into question. The element is preferably manufactured by a narrow fabric technique (i.e. as a band). The needle is preferably of stainless steel.

The needle system is attached to the end of the band section of the bioabsorbable band. The intermediate element may form a loop through the needle eye, and in that case the opposite sides of the loop are attached together or to the band. A band having a polymeric intermediate element can be attached by the compression moulding, and a band having a metallic intermediate element can be attached by the spot welding. Besides the use with the bioabsorbable band, the needle system can be used in other applications requiring a flexible needle system.

DETAILED DESCRIPTION

Figure 1A:
FIG. 1a shows a schematic side view of a bioabsorbable band and a locking member.
Figure 1B:
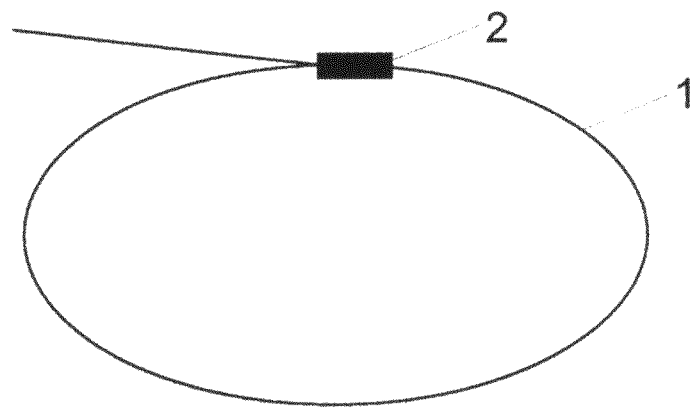
FIG. 1b shows a schematic side view of a bioabsorbable band and a locking member when the band is tightened.

FIG. 1a shows a schematic side view of a bioabsorbable band 1 and a locking member 2 before use. FIG. 1b shows a schematic side view of a bioabsorbable band 1 and a locking member 2 when they are in use. The bioabsorbable band 1 comprises a band section and a locking section. The band section is in practice the flat band-like part of the band 1 and the locking section comprises locking means. The band 1 forms a loop around a bone (not shown) and it is tightened by threading the band 1 through the locking member 2 which is placed on the locking section of the band 1.

Figure 2A:
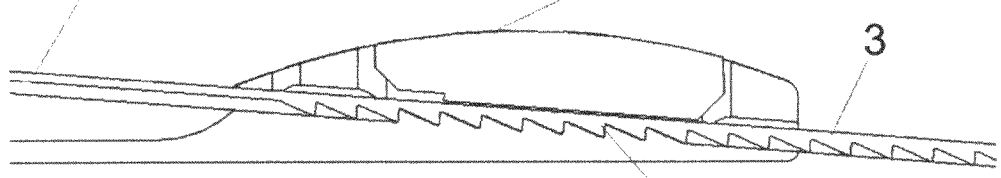
FIG. 2a shows a cross-section of a band and a locking member according to the first embodiment in the longitudinal direction of the band.

FIG. 2a shows according to the first embodiment a cross-section of a band 1 and a locking member 2 in the longitudinal direction of the band 1. The band section of the band 1 comprises pawl teeth 3 and the locking section of the band 1 comprises pawl teeth 4. The pawl teeth 3 of the band section and the pawl teeth 4 of the locking section are compatible with each other and the pawl teeth 3, 4 have the same dimensions and the same distance between the pawl teeth.

Figure 2B:
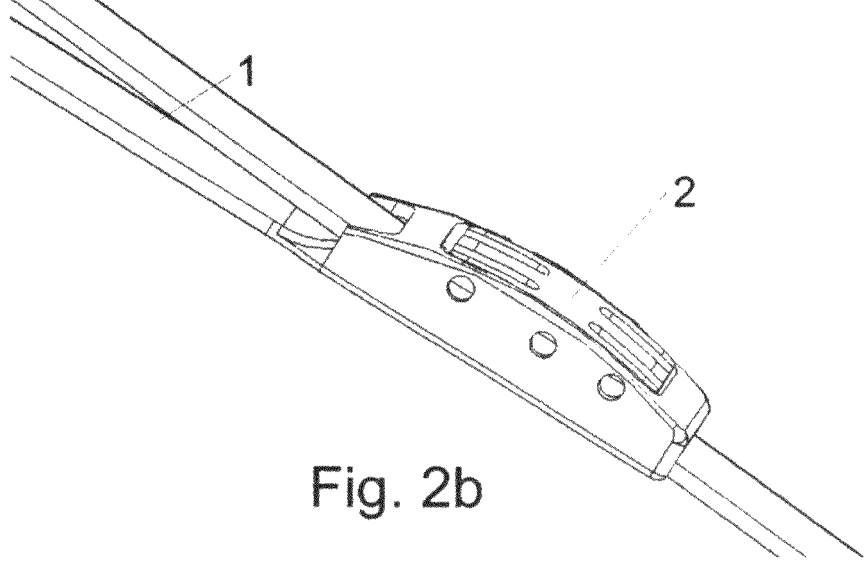
FIG. 2b shows a perspective view from the band and the locking member (in its locked position) of FIG. 2a, FIG. 2c shows the locking member of FIG. 2a in its opened position.
Figure 2C:
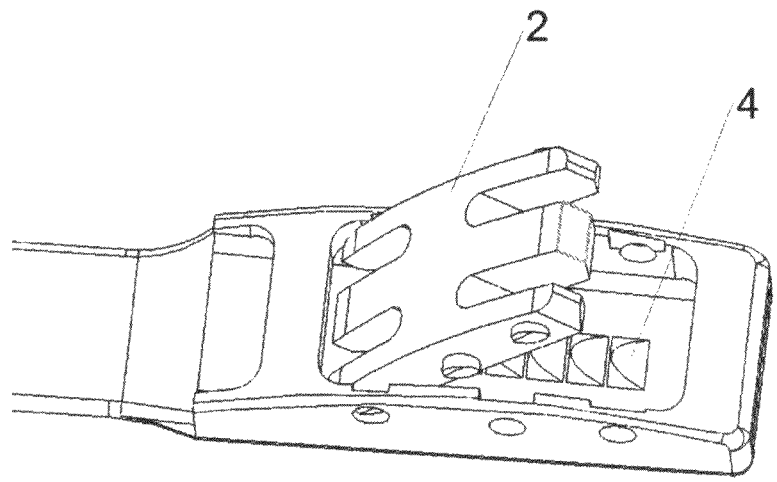

FIG. 2b shows a perspective view from the band 1 and the locking member 2 (in its locked position) of FIG. 2a, and FIG. 2c shows the locking member 2 of FIG. 2a in its opened position. The locking member 2 comprises a flap which locks the band 1 into its final position. Under the flap there are the pawl teeth 4 of the locking section.

Figure 3A:
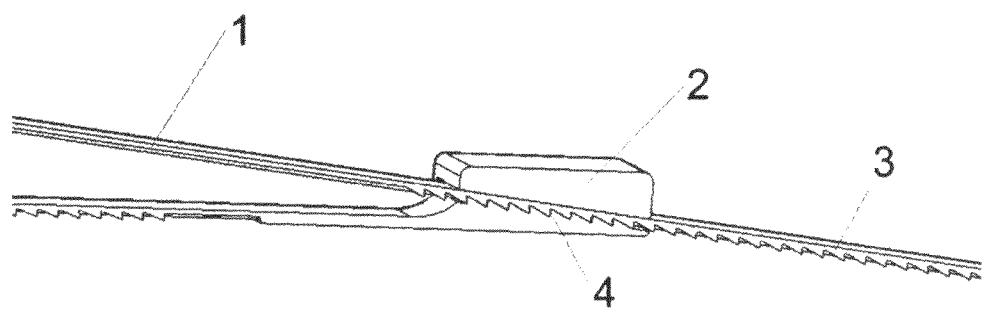
FIG. 3a shows according to the second embodiment a perspective view of the cross-section of a band and a locking member in the longitudinal direction of the band (in its locked position)
Figure 3B:
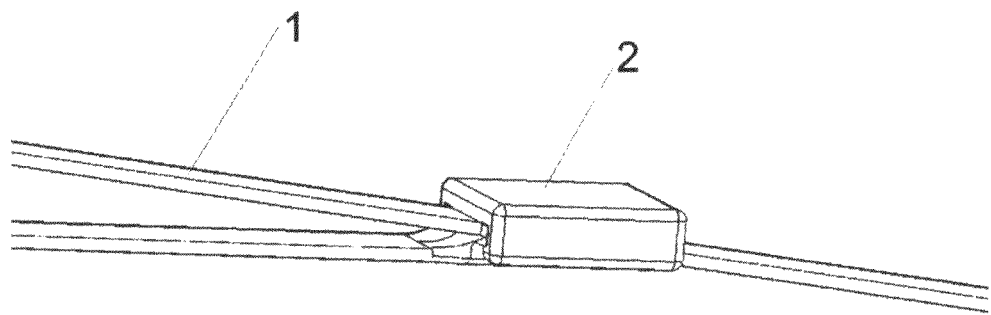
FIG. 3b shows a perspective view from the band and the locking member (in its locked position) of FIG. 3a, FIG. 3c shows the locking member of FIG. 3a in its opened position.
Figure 3C:
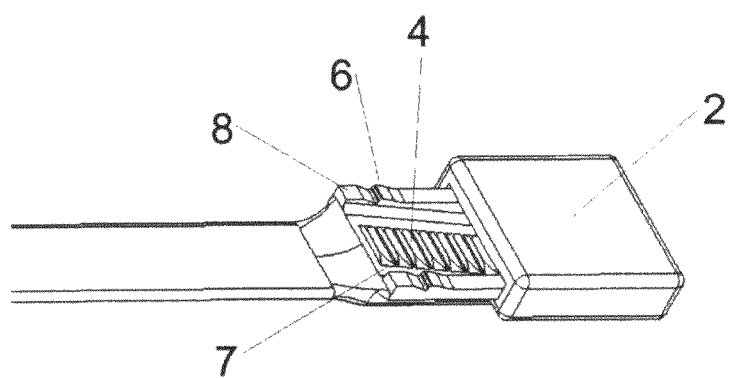

FIG. 3a shows according to the second embodiment a perspective view of the cross-section of a band 1 and a locking member 2 in the longitudinal direction of the band 1. FIG. 3b shows a perspective view from the band 1 and the locking member 2 (in its locked position) of FIG. 3a, and FIG. 3c shows the locking member of FIG. 3a in its opened position. The locking member 2 is a separate piece which can be inserted on the locking section in such a manner that it locks the first and second locking means to each other. The locking section comprises guide ribs 6 in the longitudinal direction of the band in such a manner that at least one guide rib 6 is located in each side of the locking section. The guide ribs 6 are integrated into the locking section of the band 1. Between the guide ribs 6 there is a slot 7 in which the other end of the band 1 can be inserted when the bioabsorbable band 1 is tightened. The bottom part of the slot 7 is provided with pawl teeth 4, and the bottom part is wedge-shaped in such a manner that the thickness of the bottom part increases towards the other end of the band in the longitudinal direction of the band 1.

The guide ribs 6 are compatible with grooves (not shown) in the locking member 2, and the locking member 2 can be glided into its locked position along the guide ribs 6. In the bottom of the grooves there are first gripping members (not shown), such as teeth or protrusions or both, which cooperate with second gripping members 8, such as teeth or protrusions or both, on the upper surfaces of the guide ribs in order to lock the locking member 2. The inner surface of the upper part of the locking member 2 is also wedge-shaped but its thickness increases to the opposite direction compared to the bottom part of the slot 7.

Figure 4A:
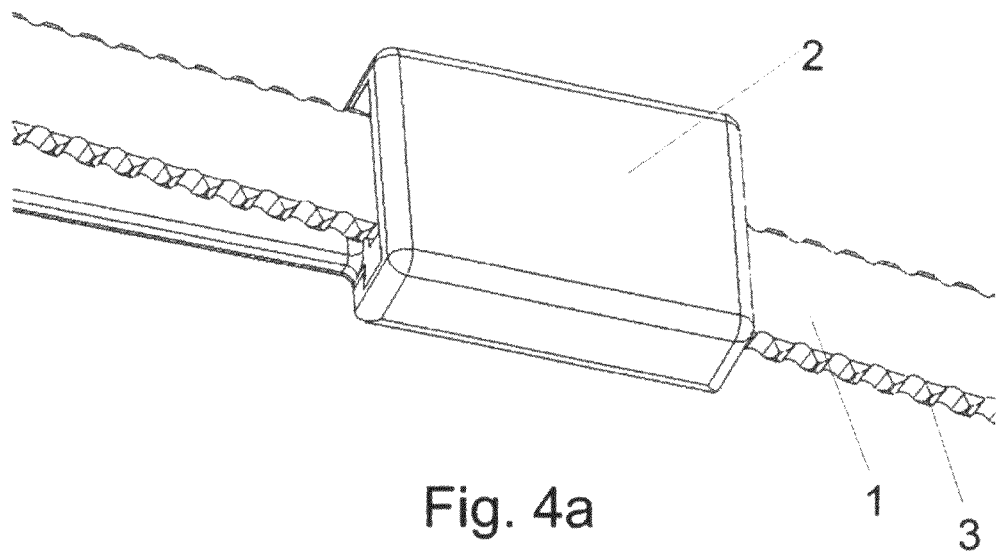
FIG. 4a shows according to the third embodiment a perspective view of a band and a locking member in its locked position.
Figure 4B:
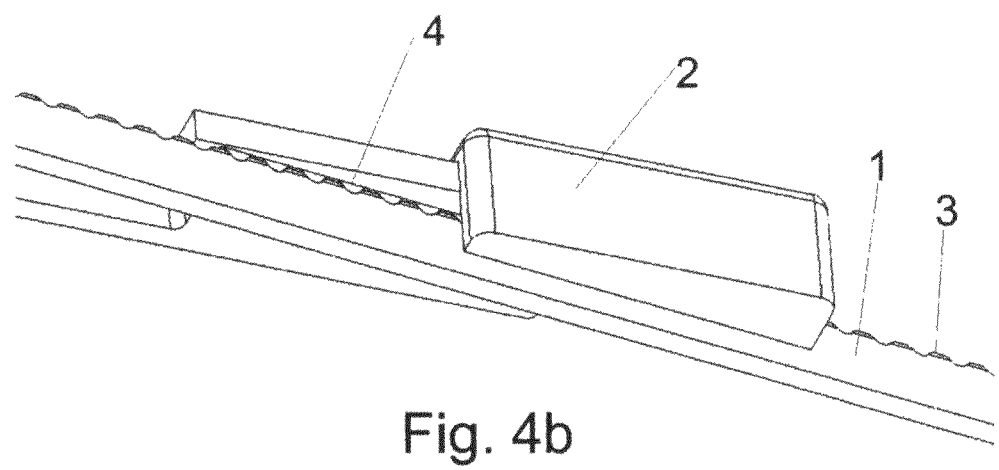
FIG. 4b shows a perspective view of the cross-section of a band and a locking member of FIG. 4a in the longitudinal direction of the band.
Figure 4C:
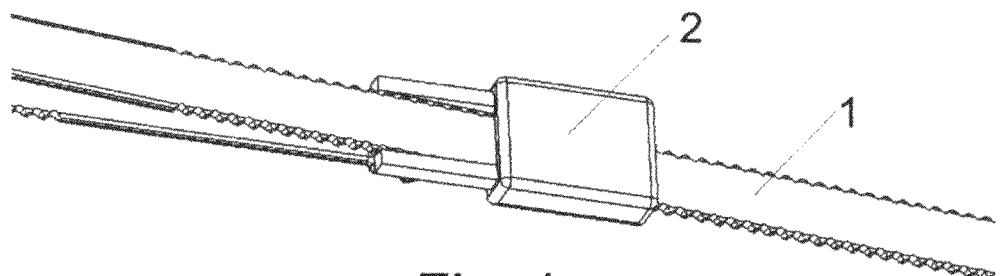
FIG. 4c shows a perspective view of the band and the locking member of FIG. 4a, FIG. 5a shows according to the fourth embodiment of the invention a band and a locking member in its locked position.

FIG. 4a shows according to the third embodiment a perspective view of a band 1 and a locking member 2 in its locked position, FIG. 4b shows a perspective view of the cross-section of a band 1 and a locking member 2 of FIG. 4a in the longitudinal direction of the band, and FIG. 4c shows a perspective view of the band 1 and the locking member 2 of FIG. 4a. The band 1 comprises pawl teeth 3 at its both longitudinal edges. The pawl teeth 3 are compatible with the pawl teeth 4 of a locking section. The locking member 2 locks the band 1 into its final position.

Figure 5A:
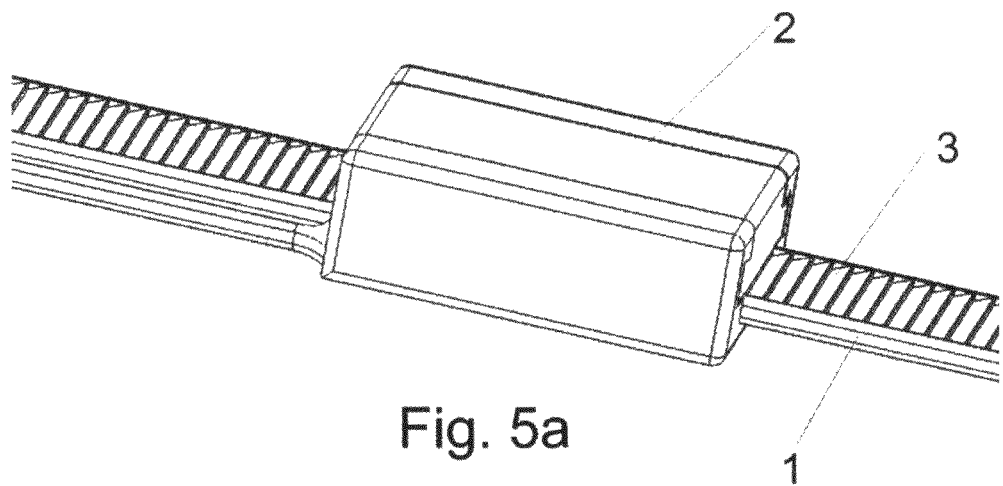
FIG. 5b shows the band and the locking member of FIG. 5a in its open position.
Figure 5B:
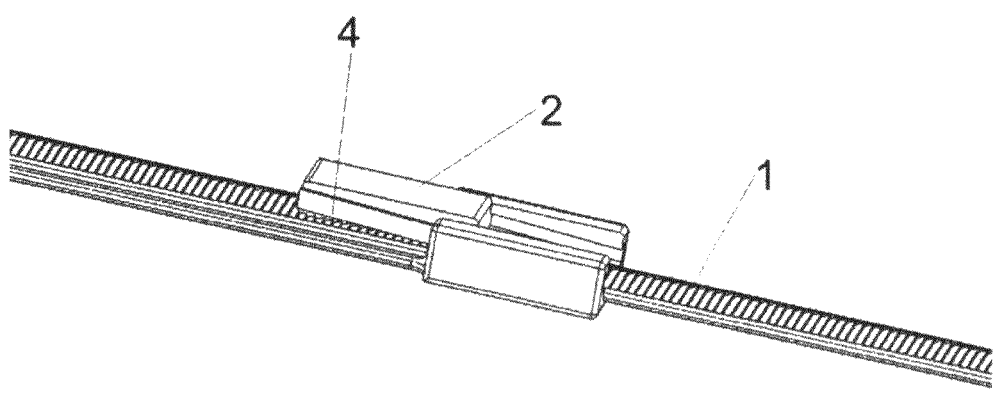

FIG. 5a shows according to the fourth embodiment of the invention a band 1 and a locking member 2 in its locked position, and FIG. 5b shows the band 1 and the locking member 2 of FIG. 5a in its open position. In the fourth embodiment pawl teeth 3 of the band are on the upper surface of the band 1 and pawl teeth 4, which are compatible with the pawl teeth 3, are located on the lower surface of the locking member 2.

Figure 6:
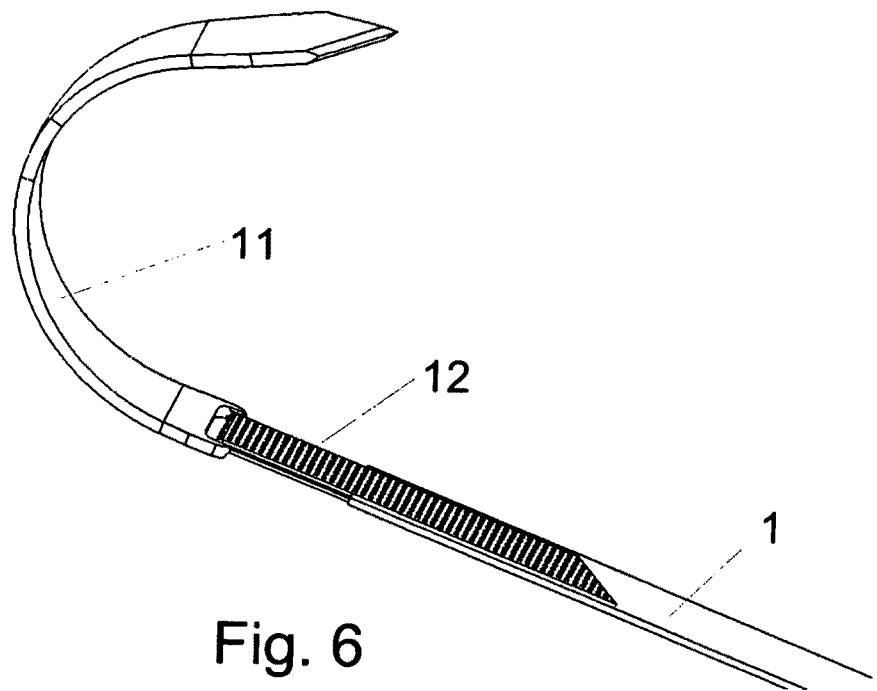
FIG. 6 shows a needle system in a perspective view.

FIG. 6 shows a needle system in a perspective view. The needle system comprises a needle 11 and an intermediate element 12. The intermediate element 12 has two ends. The first end of the intermediate element 12 is connected to the needle 11, and the second end is attached to a bioabsorbable band 1. The intermediate element 12 is flexible, thus giving a movement freedom to the needle 11 and the band 1. When the needle 11 and the band 1 are able to move in relation to each other, the concentration of stress to the band 1 or the needle 11 is avoided because the intermediate element 12 is able to deform. The element 12 may comprise a metallic mesh, or a polymeric fabric. The side edges of the element 12 are preferably smooth in such a manner that loose ends of threads do not protrude from the edges. The element is preferably manufactured by a narrow fabric technique (i.e. as a band). The needle is preferably of stainless steel.

Figure 7A:
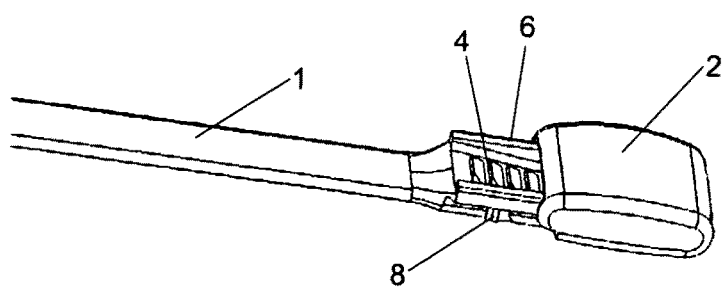
FIG. 7a shows according to the fifth embodiment of the invention a band and a locking member in its open position from above.
Figure 7B:
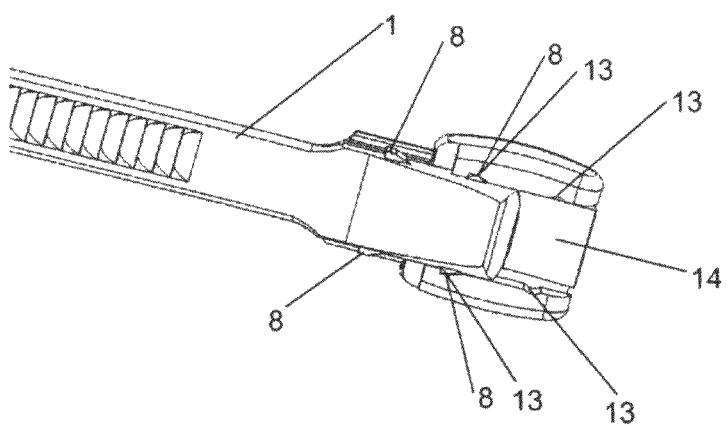
FIG. 7b shows according to the fifth embodiment of the invention a band and a locking member in its open position from under.

FIG. 7a shows according to the fifth embodiment a perspective view of a band 1 (partially) and a locking member 2 from above. FIG. 7b shows a perspective view from the band 1 and the locking member 2 from under. In both figures the locking member is in its opened position. The locking member 2 is a separate piece which can be inserted on the locking section in such a manner that it locks the first and second locking means to each other. The locking member 2 can be attached to the band 1 so that it is pre-installed before implanting to a position which is shown in FIGS. 7a and 7b.

The locking section comprises guide ribs 6 in the longitudinal direction of the band in such a manner that at least one guide rib 6 is located in each side of the locking section. The guide ribs 6 are integrated into the locking section of the band 1. Between the guide ribs 6 there is a slot 7 in which the other end of the band 1 can be inserted when the bioabsorbable band 1 is tightened. The bottom part of the slot 7 is provided with pawl teeth 4, and the bottom part is wedge-shaped in such a manner that the thickness of the bottom part increases towards the other end of the band in the longitudinal direction of the band 1.

The guide ribs 6 are compatible with grooves (not shown) in the locking member 2, and the locking member 2 can be glided into its locked position along the guide ribs 6. In the bottom of the locking member 2 there are first gripping members 13, such as recesses, which cooperate with second gripping members 8, such as teeth or protrusions or both, on the side surfaces of the guide ribs in order to lock the locking member 2. When the first gripping means 13 comprise recesses and the second gripping means comprise protrusions, the recess and the protrusion which lock the locking member in the pre-installed position are smaller than the recess and the protrusion which lock the locking member 2 in its locked position.

The inner surface 14 of the upper part of the locking member 2 is also wedge-shaped but its thickness increases to the opposite direction compared to the bottom part of the slot 7.

EXAMPLE

70L/30D,L polylactide (inherent viscosity 6.2 dl/g) is injection moulded to form a band preform. The locking section of the band is heated to 30° C. (which is below the glass transition temperature $T_g$=55° C.), and the band section of the band is heated to 75° C. The band section is drawn by a draw ratio of 1:5. A compression moulding process is used for finishing the band, for example for forming the pawl teeth. The stainless steel needle is attached to the end of the band section by compression moulding at 75° C. a flexible stainless steel mesh in to the band and passing the mesh through the eye hole at the end of the needle.

The invention claimed is:

1. A bioabsorbable band system for securing a bone fracture, or an osteotomy, or a soft tissue on a bone, the bioabsorbable band system, comprising:
   a needle system; and
   a bioabsorbable band including a bioabsorbable band section comprising a first lock and a bioabsorbable locking section comprising a second lock and a locking member,
   wherein the band section comprises a length having an at least partially oriented structure said oriented structure having been formed by drawing and having a predetermined draw ratio,
   wherein the band section and locking section have different draw ratios and a length having an orientation gradient at a junction of the band section and the locking section,
   wherein the first lock is configured to grip the second lock of the locking section to form a locking, and
   wherein the locking member is configured to secure the locking.

2. A bioabsorbable band for securing a bone fracture, or an osteotomy, or a soft tissue on a bone, the band comprising:
   a bioabsorbable locking section; and
   a bioabsorbable band section comprising a first lock and a bioabsorbable locking section comprising a second lock and a locking member,
   wherein the band section comprises a length having an at least partially oriented structure, said at least partially oriented structure having been formed by drawing and having a predetermined draw ratio,
   wherein the band section and locking section have different draw ratios and a length having an orientation gradient at the junction of the band section and the locking section,
   wherein the first lock is configured to grip the second lock of the locking section to form a locking, and
   wherein the locking member is configured to secure the locking.

3. The bioabsorbable band according to claim 2, wherein the draw ratio of the orientation is between 1:1.1 and 1:10.

4. The bioabsorbable band according to claim 1, wherein the first and the second locks comprise pawl teeth.

* * * * *

UNITED STATES PATENT AND TRADEMARK OFFICE
CERTIFICATE OF CORRECTION

| | | |
|---|---|---|
| PATENT NO. | : 8,512,379 B2 | Page 1 of 1 |
| APPLICATION NO. | : 11/988937 | |
| DATED | : August 20, 2013 | |
| INVENTOR(S) | : Heino et al. | |

It is certified that error appears in the above-identified patent and that said Letters Patent is hereby corrected as shown below:

On the Title Page, Item (30) should read:

(30)   Foreign Application Priority Data

July 18, 2005    (FI) .................................... 20055416

Signed and Sealed this
Twenty-second Day of October, 2013

Teresa Stanek Rea
*Deputy Director of the United States Patent and Trademark Office*